United States Patent
Hara et al.

(10) Patent No.: US 7,501,282 B2
(45) Date of Patent: Mar. 10, 2009

(54) **PLASMID AUTONOMOUSLY REPLICABLE IN *ENTEROBACTERIACEAE* FAMILY**

(75) Inventors: Yoshihiko Hara, Kawasaki (JP); Hiroshi Izui, Kawasaki (JP); Hiromi Noguchi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 349 days.

(21) Appl. No.: 11/276,334

(22) Filed: Feb. 24, 2006

(65) Prior Publication Data

US 2006/0246552 A1 Nov. 2, 2006

Related U.S. Application Data

(60) Provisional application No. 60/659,891, filed on Mar. 10, 2005.

(30) Foreign Application Priority Data

Feb. 25, 2005 (JP) ............... 2005-051163

(51) Int. Cl.
- C12N 15/74 (2006.01)
- C12N 1/21 (2006.01)
- C12N 15/52 (2006.01)
- C12P 13/04 (2006.01)

(52) U.S. Cl. .......... 435/476; 435/252.3; 435/320.1; 435/106; 536/23.1

(58) Field of Classification Search .......... None
See application file for complete search history.

(56) References Cited

U.S. PATENT DOCUMENTS

| | | | |
|---|---|---|---|
| 6,197,559 B1 | 3/2001 | Moriya et al. | |
| 6,331,419 B1 | 12/2001 | Moriya et al. | |
| 6,596,517 B2 | 7/2003 | Izui et al. | |
| 6,653,110 B2 | 11/2003 | Sato et al. | |
| 6,706,522 B1 * | 3/2004 | Blattner et al. ............ | 435/320.1 |
| 2005/0196846 A1 | 9/2005 | Hara et al. | |
| 2006/0040365 A1 | 2/2006 | Rybak et al. | |
| 2006/0088919 A1 | 4/2006 | Rybak et al. | |
| 2006/0110813 A1 | 5/2006 | Takahashi et al. | |

FOREIGN PATENT DOCUMENTS

| | | |
|---|---|---|
| EP | 0 999 282 | 5/2000 |
| EP | 1 078 989 | 2/2001 |
| EP | 1 233 069 | 8/2002 |
| EP | 1 352 966 | 10/2003 |
| EP | 1 382 686 | 1/2004 |
| JP | 61-139398 | 6/1986 |
| WO | WO98/59054 | 12/1998 |

OTHER PUBLICATIONS

Goguen, J. D., et al., "Plasmid-Determined Cytotoxicity in *Yersinia pestis* and *Yersinia pseudotuberculosis*," Infection and Immunity 1986;51(3)::788-794.
Scholz, P., et al., "Complete nucleotide sequence and gene organization of the broad-host-range plasmid RSF1010," Gene 1989;75:271-288.
Song, Y., et al., "Complete Genome Sequence in *Yersinia pestis* Strain 91001, an Isolate Avirulent to Humans," DNA Res 2004;11:179-197.
Vieira, J., et al., "The pUC plasmids, an M13mp7-derived system for insertion mutagenesis and sequencing with synthetic universal primers," Gene 1982;19:259-268.
Youngren, B., et al., "A Plasmid Partition System of the P1-P7*par* Family from the pMT1 Virulence Plasmid of *Yersinia pestis*," J. Bacteriol. 2000;182(14):3924-3928.
International Preliminary Report on Patentability for PCT Patent App. No. PCT/JP2006/304040 (Sep. 7, 2007).
Database UniProt[Online], "Replication protein repA," Entry name: REPA SALTI, XP002384658 (2001).
Database UniProt [Online], "Replication protein A," Entry name: Q7ARD4 YERPE, XP002384659 (2004).
Tait, R. C., et al., "A Comparison of the Origin of Replication of pSa with R6K," Mol. Gen. Genet. 1983;192:32-38.
International Search Report and Written Opinion of the International Searching Authority for PCT Patent App. No. PCT/JP2006/304040 (Jul. 6, 2006).

* cited by examiner

*Primary Examiner*—Nancy Vogel
(74) *Attorney, Agent, or Firm*—Shelly Guest Cermak; Cermak Kenealy Vaidya & Nakajima LLP

(57) ABSTRACT

A gene isolated from a microorganism selected from the group consisting of *Pantoea* bacteria, *Erwinia* bacteria, and *Enterobacter* bacteria, and encoding a Rep protein or a homologue thereof is described. A plasmid containing the gene which is autonomously replicable in Enterobacteriaceae bacteria is also described. A Enterobacteriaceae microorganism containing the plasmid is also described.

14 Claims, 4 Drawing Sheets

PLASMID AUTONOMOUSLY REPLICABLE IN ENTEROBACTERIACEAE FAMILY

CROSS REFERENCE TO RELATED APPLICATIONS

This application claims priority under 35 U.S.C. §119(a) to JP2005-051163, filed Feb. 25, 2005, and under 35 U.S.C. §119(e) to U.S. application 60/659,891, filed Mar. 10, 2005, the entireties of both are incorporated by reference. The Sequence Listing on Compact Disk filed herewith is also hereby incorporated by reference in its entirety (File Name: US-220 Seq List; File Size: 10 KB; Date Created: Feb. 24, 2006)

BACKGROUND OF THE INVENTION

1. Field of the Invention

The present invention relates to a novel plasmid which is autonomously replicable in a microorganism from the family Enterobacteriaceae, and methods for utilizing the plasmid and a microorganism containing the plasmid.

2. Brief Description of the Related Art

At present, breeding and improving microorganisms from the family Enterobacteriaceae, including *Escherichia coli*, by DNA recombination techniques are progressing. In order to breed and improve microorganisms by DNA recombination techniques, a plasmid derived from a microorganism of a different genus and a broad host spectrum vector are often used. However, a plasmid from a microorganism which has similar properties is generally used.

Plasmids derived from microorganisms from the family Enterobacteriaceae include small plasmids such as pBR322, RSF1010 (Gene, vol. 75, (2) pp. 271-288, 1989), and pUC (Gene, October 1982, 19(3):259-68) all of which are derived from *Escherichia coli*, pHCM2 derived from *Salmonella* bacteria (Plasmid, May 2002, 47(3):159-71), pCD1 (Infect. Immun., March 1986, 51(3):788-94) and pMT1 (J. Bacteriol., July 2000, 182 (14):3924-8) both of which are derived from *Yersinia* bacteria, and so forth. Although pS is known to be from *Pantoea* bacteria (WO98/59054), a plasmid which can improve the growth of a microorganism under acidic conditions when transferred into the microorganism has not been previously reported.

SUMMARY OF THE INVENTION

It is an object of the present invention to provide a novel plasmid which is useful for breeding and improving microorganisms belonging to the family Enterobacteriaceae.

The inventors of the present invention found that *Pantoea ananatis* AJ13601 (FERM BP-7207) harbors a novel plasmid and successfully identified this plasmid. Thus, they accomplished the present invention.

It is an object of the present invention to provide a gene derived from a microorganism selected from the group consisting of *Pantoea* bacteria, *Erwinia* bacteria, and *Enterobacter* bacteria, and wherein said gene encodes a Rep protein having an amino acid sequence selected from the group consisting of SEQ ID NO: 2 and an amino acid sequence which is at least 80% homologous to SEQ ID NO: 2.

It is a further object of the present invention to provide a plasmid comprising the gene as defined above, and wherein said plasmid is autonomously replicable in Enterobacteriaceae bacteria.

It is a further object of the present invention to provide the plasmid as described above, wherein said plasmid further comprises a marker gene.

It is a further object of the present invention to provide the plasmid as described above, wherein the plasmid is from a *Pantoea* bacterium selected from the group consisting of *Pantoea ananatis* FERM BP-7207, BP-6614 and BP-6615, and is about 320 kbs.

It is a further object of the present invention to provide the plasmid as described above, wherein the plasmid is pEA320, and has a restriction enzyme map selected from the group consisting of those shown in FIGS. 1, 2, 3, 4, and 5.

It is a further object of the present invention to provide an Enterobacteriaceae microorganism which has been transformed with a plasmid comprising a gene isolated from a microorganism selected from the group consisting of *Pantoea* bacteria, *Erwinia* bacteria, and *Enterobacter* bacteria, and wherein said gene encodes a Rep protein having an amino acid sequence selected from the group consisting of SEQ ID NO: 2 and an amino acid sequence which is at least 80% homologous to SEQ ID NO: 2.

It is a further object of the present invention to provide the microorganism as described above, wherein the plasmid is from a *Pantoea* bacterium selected from the group consisting of *Pantoea ananatis* FERM BP-7207, BP-6614 and BP-6615 and is about 320 kbs.

It is a further object of the present invention to provide the microorganism as described above, wherein the plasmid is pEA320 and has a restriction enzyme map selected from the group consisting of those shown in FIGS. 1, 2, 3, 4, and 5.

It is a further object of the present invention to provide the microorganism as described above, wherein the plasmid further comprises a marker gene and is autonomously replicable in an Enterobacteriaceae microorganism.

It is a further object of the present invention to provide the microorganism as described above, wherein the Enterobacteriaceae microorganism is selected from the group consisting of *Escherichia* bacteria, *Pantoea* bacteria, *Enterobacter* bacteria, *Erwinia* bacteria, *Klebsiella* bacteria, *Serratia* bacteria, *Salmonella* bacteria, and *Morganella* bacteria.

It is a further object of the present invention to provide the microorganism as described above, which is able to produce a useful substance.

It is a further object of the present invention to provide a method for producing a useful substance comprising culturing the microorganism as described above in a medium, and collecting the useful substance from the medium or the microorganism.

It is a further object of the present invention to provide the method as described above, wherein the useful substance is an L-amino acid.

It is a further object of the present invention to provide a method for producing a microorganism with improved acid resistance comprising transforming an Enterobacteriaceae microorganism with the plasmid as described above.

It is further object of the present invention to provide a method as described above, wherein the microorganism with improved acid resistance shows improved growth at a pH of 3 to 5, as compared with a strain not containing the plasmid.

DETAILED DESCRIPTION OF EXEMPLARY EMBODIMENTS

Figure 1:
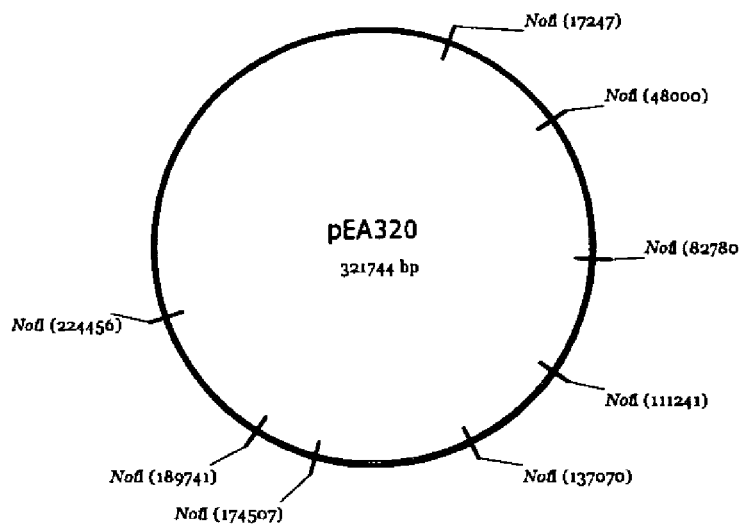
FIG. 1 shows a restriction enzyme map of the plasmid pEA320 for NotI.
Figure 2:
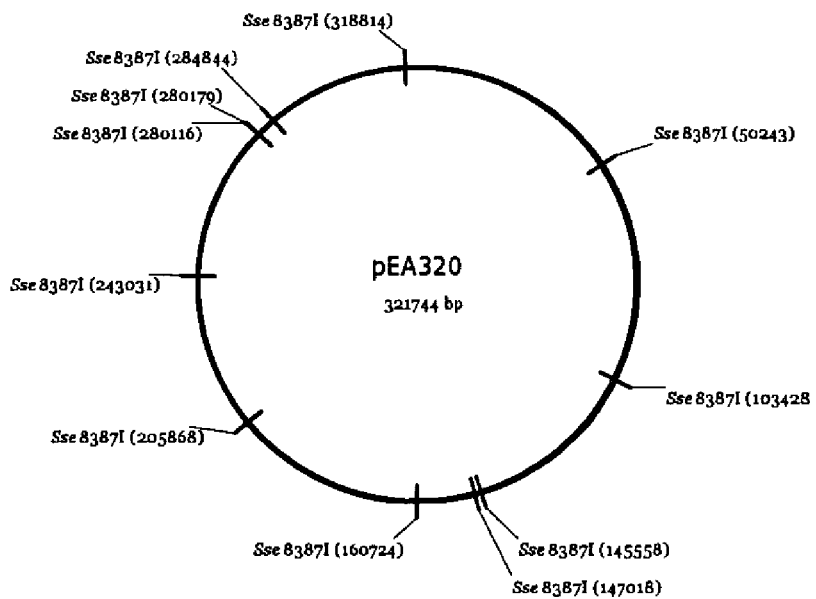
FIG. 2 shows a restriction enzyme map of the plasmid pEA320 for Sse83871.
Figure 3:
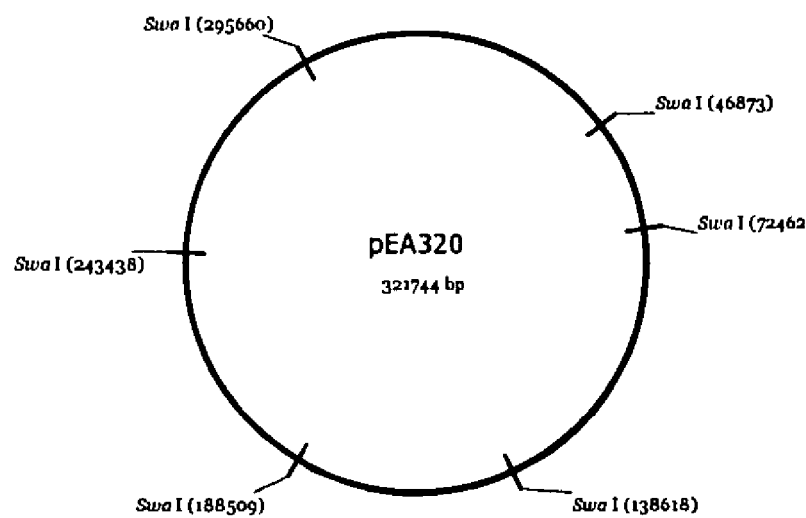
FIG. 3 shows a restriction enzyme map of the plasmid pEA320 for SwaI.
Figure 4:
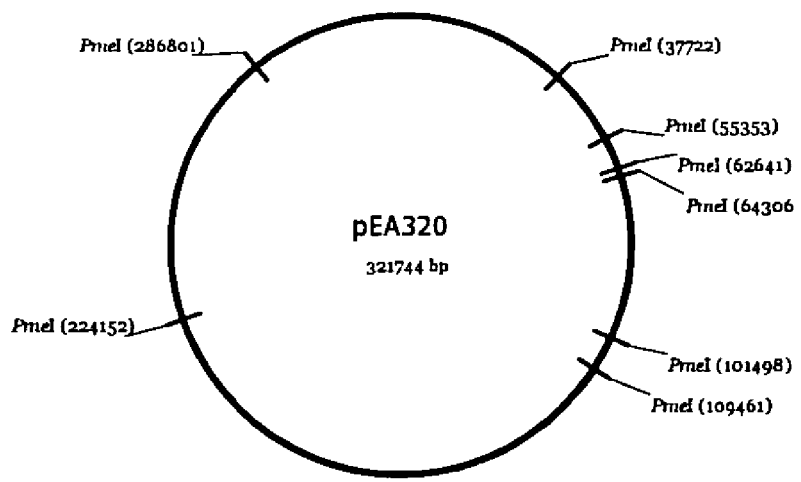
FIG. 4 shows a restriction enzyme map of the plasmid pEA320 for PmeI.
Figure 5:
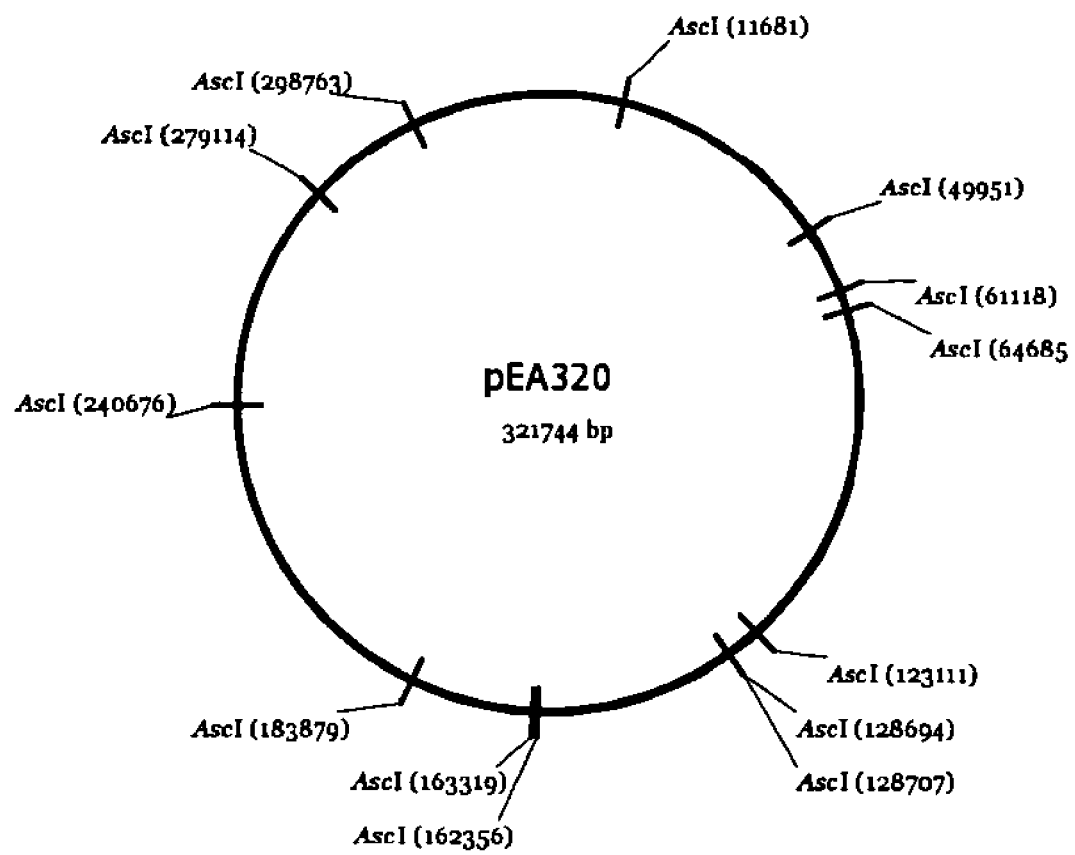
FIG. 5 shows a restriction enzyme map of the plasmid pEA320 for AscI.

Hereinafter, the present invention will be explained in detail.

<1> Gene and Plasmid of the Present Invention

The gene of the present invention is a gene which is derived or isolated from *Pantoea* bacteria, *Erwinia* bacteria, or *Enterobacter* bacteria. This gene encodes a Rep protein having the amino acid sequence of SEQ ID NO: 2, or an amino acid sequence which is at least 80% homologous to SEQ ID NO: 2 (rep gene). The plasmid of the present invention contains the gene of the present invention.

The gene of the present invention was identified by analyzing the pEA320 plasmid. pEA320 is about 320 kbs and is derived or isolated from a bacterium such as *Pantoea ananatis* AJ13601 (FERM BP-7207), *Pantoea ananatis* AJ 13355(FERM BP-6614), or *Pantoea ananatis* AJ 13356(FERM BP-6615), as will be described later. *Pantoea* bacteria, *Erwinia* bacteria, and *Enterobacter* bacteria are microorganisms classified as γ-proteobacteria, and they are taxonomically very similar to one another (J. Gen. Appl. Microbiol., December 1997, 43(6), 355-361; International Journal of Systematic Bacteriology, 1993, pp. 162-173; and International Journal of Systematic Bacteriology, October 1997, pp. 1061-1067). Recently, some microorganisms from the genus *Enterobacter* were re-classified as *Pantoea agglomerans*, *Pantoea ananatis*, *Pantoea stewartii*, or the like, on the basis of nucleotide sequence analysis of 16S rRNA etc., and some microorganisms from the genus *Erwinia* were re-classified into *Pantoea ananas* or *Pantoea stewartii* (refer to International Journal of Systematic Bacteriology, October 1997, pp. 1061-1067).

Furthermore, they commonly show the following physiological properties (U.S. Pat. Nos. 6,331,419 and 6,197,559):

(1) Gram stain: Negative
(2) Behavior for oxygen: Facultative anaerobe
(3) Voges-Proskauer reaction: Positive
(4) Methyl Red test: Negative
(5) Indole production: Positive
(6) β-Galactosidase: Positive
(7) Sugar assimilability:
Arabinose: Positive
Sucrose: Positive
Lactose: Positive
Xylose: Positive
Sorbitol: Positive
Inositol: Positive
Trehalose: Positive
Maltose: Positive
Melibiose: Positive
Adonitol: Negative
Raffinose: Positive
Salicin: Negative
Melibiose: Positive (8) Citric acid assimilability: Positive
(9) Arginine dehydratase: Negative
(10) Ornithine decarboxylase: Negative
(11) Growth pH: Good growth at pH 4.5 to 7

Therefore, the gene of the present invention can be obtained from a giant plasmid which is native to *Pantoea* bacteria, *Erwinia* bacteria, and *Enterobacter* bactera, particularly a giant plasmid obtained from a wild-type strain of such bacteria. Typical strains of the *Pantoea* bacteria which contain such a giant plasmid include *Pantoea ananatis*, *Pantoea stewartii*, and *Pantoea agglomerans*. Typical strains of such *Erwinia* bacteria include *Erwinia ananas* and *Erwinia herbicola*. Finally, typical strains of such *Enterobacter* bacteria include *Enterobacter agglomerans* and *Enterobacter aerogenes*.

In addition, some strains of *Enterobacter agglomerans* were recently re-classified as *Pantoea agglomerans*, *Pantoea ananatis*, *Pantoea stewartii*, or the like, on the basis of nucleotide sequence analysis of 16S rRNA etc. In the present invention, the gene and the plasmid may be derived or isolated from one of *Enterobacter*, *Pantoea*, and *Erwinia* so long as the microorganism is classified as Enterobacteriaceae. When a *Pantoea ananatis* strain is bred by a genetic engineering technique, *Pantoea ananatis* AJ13355 strain (FERM BP-6614), AJ13356 strain (FERM BP-6615), AJ13601 strain (FERM BP-7207), and derivatives thereof can be used. These strains were identified as *Enterobacter agglomerans* when they were isolated and deposited as *Enterobacter agglomerans*. However, they were recently re-classified as *Pantoea ananatis* on the basis of nucleotide sequencing of 16S rRNA and so forth.

Specifically, the gene of the present invention can be obtained from the *Pantoea ananatis* AJ13601 (FERM BP-7207) strain (EP1078989A). The *Pantoea ananatis* AJ13601 strain was deposited at the National Institute of Bioscience and Human-Technology, Agency of Industrial Science and Technology, Ministry of Economy, Trade and Industry (currently, the International Patent Organism Depositary, National Institute of Advanced Industrial Science and Technology, address: Tsukuba Central 6, 1-1, Higashi 1-Chome, Tsukuba-shi, Ibaraki-ken, 305-8566, Japan) on Aug. 18, 1999 and given an accession number of FERM P-17516. The deposit was converted to an international deposition under the provisions of the Budapest Treaty on Jul. 6, 2000 and given an accession number of FERM BP-7207.

Furthermore, the gene of the present invention can also be obtained from *Erwinia ananas* and *Erwinia herbicola*. Examples of *Erwinia ananas* include *Erwinia ananas* ATCC 33244 and *Erwinia herbicola* IAM1595. The ATCC 33244 strain can be obtained from the American Type Culture Collection (Address: P.O. Box 1549, Manassas, Va. 20108, United States of America) using the assigned registration number (refer to www.atcc.org/). The registration numbers for each strain are also listed in the catalog of the American Type Culture Collection. IAM1595 is stored at the IAM Culture Collection, Laboratory of Bioresources, Institute of Molecular and Cellular Biosciences, The University of Tokyo, and it can be ordered by the registration number. The registration numbers for each strain are listed in the IAM catalog (IAM Catalogue of Strain, Third Edition, 2004).

Furthermore, the gene of the present invention can also be obtained from *Enterobacter agglomerans* and *Enterobacter aerogenes*. An example of *Enterobacter agglomerans* is ATCC 12287 and an example of *Enterobacter aerogenes* is ATCC 13048.

The aforementioned *Pantoea ananatis* was found to contain a plasmid of about 320 kbs, which was identified and designated pEA320. This plasmid exists as a double-stranded cyclic DNA in the cells of *Pantoea ananatis*. The nucleotide sequence of the rep gene contained in pEA320 is shown as SEQ ID NO: 1, and the amino acid sequence is shown as SEQ ID NO: 2.

The numbers and sizes of fragments obtained from pEA320 when digested with typical restriction enzymes are shown in Table 1. Furthermore, restriction enzyme maps of pEA320 are shown in FIGS. 1 to 5. The gene encoding the rep protein is located from 110606 to 109728 on the enzyme maps of pEA320.

TABLE 1

| Restriction enzyme | Number of cleavage sites | Position of cleavage sites |
|---|---|---|
| AscI | 13 | 11681 49951 61118 64685 123111 128694 128707 162356 163319 183879 240676 279114 298763 |
| NotI | 8 | 17247 48000 82780 111241 137070 174507 189741 224456 |
| PmeI | 8 | 37722 55353 62641 64306 101498 109461 224152 286801 |
| Sse8387I | 11 | 50243 103428 145558 147018 160724 205868 243031 280116 280179 284844 318814 |
| SwaI | 6 | 46873 72462 138618 188509 243438 295660 |

The Rep protein encoded by the gene of the present invention is defined as having the amino acid sequence of SEQ ID NO: 2, or a homologue thereof. The amino acid sequence of this Rep protein (SEQ ID NO: 2) and the amino acid sequences of the Rep proteins of the plasmids of known Enterobacteriaceae bacteria were compared to determine homology. Thus, the gene of the present invention can be distinguished from the genes of known Enterobacteriaceae bacteria by comparing the homology of the encoded Rep proteins. The gene of the present invention includes a homologue which encodes a Rep protein having homology of 80% or higher, preferably 90% or higher, more preferably 95% or higher, most preferably 97% or higher, with respect to the total amino acid sequence of SEQ ID NO: 2, and wherein said protein or homologue is involved in the replication of the plasmid. Homology, as calculated herein, is analyzed and calculated using the gene analysis software Genetyx (which can be purchased from Genetyx, Inc.), and indicates the ratio of exactly matching amino acid residues. Homologies (identities) of amino acid sequences and nucleotide sequences can be determined by using, for example, the algorithm BLAST by Karlin and Altschul (Pro. Natl. Acad. Sci. USA, 90, 5873 (1993)) or FASTA (Methods Enzymol., 183, 63 (1990)). Programs called BLASTN and BLASTX have been developed on the basis of this algorithm BLAST (refer to www.ncbi.nlm.nih.gov).

Furthermore, differences may exist in the nucleotide sequences of the rep genes depending on the species or strains of the *Pantoea, Erwinia*, and *Enterobacter* bacteria. Therefore, the Rep protein may have an amino acid sequence which includes substitution, deletion, insertion, or addition of one or several amino acid residues, so long as the the Rep protein function is not changed by this variance. The substitution, deletion, insertion, or addition of amino acids may be, for example, 1 to 20, preferably 1 to 10, more preferably 1 to 5. The aforementioned substitution, deletion, insertion or addition of amino acid residues is conservative, and will not effect the normal replication of the plasmid. A typical conservative amino acid change is a conservative substitution. For example, substitutions considered to be conservative include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

Furthermore, the gene encoding the Rep protein may also be a DNA which is able to hybridize with the nucleotide sequence of SEQ ID NO: 1, or a probe that can be prepared from this nucleotide sequence under stringent conditions, so long as it encodes a protein which retains the function of replicating the plasmid. "Stringent conditions" include those under which a so-called specific hybrid is formed, and a non-specific hybrid is not formed. Examples of stringent conditions include, for example, those whereby, for example, DNAs having a homology of not less than 80% hybridize with each other, and DNAs showing a homology lower than 80% do not hybridize with each other. A specific example includes washing one time, preferably two or three times, at a salt concentration and a temperature of 1×SSC, 0.1% SDS and 60° C., preferably 0.1×SSC, 0.1% SDS and 60° C., more preferably 0.1×SSC, 0.1% SDS and 68° C., which are typical Southern hybridization washing conditions. Although the length of the probe is suitably chosen depending on the conditions of hybridization, it is usually 100 bps to 1 kbps.

The plasmid of the present invention, which is native to *Pantoea, Erwinia*, and *Enterobacter* bacteria, can autonomously replicate in an Enterobacteriaceae microorganism, such as *Pantoea* and *Escherichia* bacteria. Therefore, if an objective gene is inserted at any position in the plasmid, or a modified version thereof which maintains the autonomous replication ability, and a host microorganism is transformed with this recombinant plasmid, expression of the objective gene in the host microorganism is possible.

Examples of the Enterobacteriaceae microorganism which is transformed with the plasmid of the present invention include *Escherichia, Pantoea, Enterobacter, Erwinia, Klebsiella, Serratia, Salmonella*, or *Morganella* bacteria. Specifically, Enterobacteriaceae bacteria according to the classification described in the NCBI (National Center for Biotechnology Information) database can be used.

Specifically, *Escherichia* bacteria mentioned in Neidhardt et al. (Neidhardt, F. C. et al., *Escherichia coli* and *Salmonella Typhimurium*, American Society for Microbiology, Washington D.C., 1029, Table 1) can be used. Among these, *Escherichia coli* can be used, for example. Examples of *Escherichia coli* include, specifically, *Escherichia coli* W3110 (ATCC 27325), *Escherichia coli* MG1655 (ATCC 47076), and so forth, and those derived from the prototype wild-type strain, K12 strain.

Examples of *Enterobacter* bacteria include *Enterobacter agglomerans, Enterobacter aerogenes*, and so forth. Specifically, the strains exemplified in European Patent Publication No. 952221 A can be used. As described above, some strains of *Enterobacter agglomerans* were recently re-classified as *Pantoea agglomerans, Pantoea ananatis, Pantoea stewartii*, or the like, on the basis of nucleotide sequence analysis of 16S rRNA etc.

Typical strains of the *Pantoea* bacteria include *Pantoea ananatis, Pantoea stewartii, Pantoea agglomerans*, and *Pantoea citrea*. Specifically, the strains exemplified in European Patent Publication No. 955368 A can be used.

Typical strains of the *Erwinia* bacteria include *Erwinia ananas* and *Erwinia herbicola*, and typical strains of the *Klebsiella* bacteria include *Klebsiella planticola*. Specifically, the strains exemplified in European Patent Publication No. 955368 A can be used.

Typical strains of the *Serratia* bacteria include *Serratia liquefaciens*, typical strains of *Salmonella* bacteria include *Salmonella typhimurium*, and typical strains of *Morganella* include *Morganella morganii*. Specifically, as the bacteria belonging to *Serratia* bacteria, the strains exemplified in European Patent Publication No. 952221 A can be used.

The plasmid of the present invention includes a part of the giant plasmid native to *Pantoea, Erwinia*, and *Enterobacter* bacteria, and the giant plasmid itself or a part thereof and another DNA sequence, so long as the gene of the present invention is contained within the plasmid. If only a part of the giant plasmid is used, the region essential for the autonomous replication of the plasmid must be included. The plasmid can autonomously replicate in a host microorganism, even if a portion or the whole region other than the region essential for the autonomous replication of the plasmid (replication control region), for example, other than the region containing the replication origin and genes necessary for the replication, is removed, and in addition, becomes smaller by such removal. Therefore, it is preferred for use as a vector. Furthermore, if a marker gene such as a drug resistance gene is incorporated into the plasmid of the present invention, it becomes easy to detect transformants by the phenotype of the marker gene in the transformants. Examples of such a marker gene that can be used in the host include a chloramphenicol resistance gene, kanamycin resistant gene, streptomycin resistance gene, tetracycline resistence gene, erythromycin resistance gene, ampicillin resistance gene, spectinomycin resistance gene, and so forth.

As for the antibiotic resistance gene, only a region necessary for the replication of the above-described giant plasmid may be isolated and ligated to the antibiotic resistance gene, or the antibiotic resistance gene may be transferred into a portion of the giant plasmid which is not involved in replication. As the method for introducing an antibiotic resistance gene into this plasmid, the methods described in Sambrook, J., Fritsch, E. F. and Maniatis, T., "Molecular Cloning A Laboratory Manual, Second Edition", Cold Spring Harbor Laboratory Press (1989), and so forth may be used. Such methods are well known to those skilled in the art. For example, the method of using a single strand DNA developed by Datsenko and Wanner, which is called "Red-driven integration" (Proc. Natl. Acad. Sci. USA, 2000, vol. 97, No. 12, pp. 6640-6645), and the method of introducing an antibiotic resistance gene into a transposon and transferring the transposon as described in Japanese Patent Application Laid-open (Kokai) No. 2-109985 may be used.

Although pEA320, which is an example of the giant plasmid, is characterized by the restriction enzyme maps shown in FIGS. 1 to 5, the plasmid of the present invention may not necessarily have these restriction enzyme maps, and an arbitrary restriction enzyme site may be deleted so long as the autonomous replication ability is not affected. Furthermore, a restriction enzyme site which is not present in pEA320 may be introduced into the plasmid of the present invention.

Such a plasmid as described above can be prepared in the same manner as in the conventionally known preparation of a cloning vector, expression vector etc. To prepare a modified plasmid, it is preferred that the nucleotide sequence of the giant plasmid has been determined. The nucleotide sequence can be determined by known methods such as the dideoxy method.

In order to insert an objective gene into the plasmid of the present invention, it is convenient to insert it at a restriction enzyme site of the plasmid or a derivative thereof. The chosen restriction enzyme site should be unique to the plasmid, and should be cleaved by the corresponding restriction enzyme. In order to insert an objective gene, the plasmid and a genomic DNA, or the like, serving as a source of the objective gene, can be partially or fully digested with such restriction enzymes leaving corresponding sticky ends which are compatible with, for example, the same restriction enzymes, and they can be ligated under appropriate conditions. Alternatively, they may be blunt-end ligated.

Digestion and ligation of DNA, transformation, and so forth, and usual methods well known to those skilled in the art can be used to prepare the plasmid DNA. Such methods are described in Sambrook, J., Fritsch, E. F. and Maniatis, T., "Molecular Cloning A Laboratory Manual, Second Edition", Cold Spring Harbor Laboratory Press (1989), and so forth. To extract the giant plasmid, the method described in J. Bacteriol, March 1981, Vol. 145, No. 3, pp. 1365-1373 can be used.

The plasmid of the present invention can also be transferred from a microorganism which contains the plasmid of the present invention into another microorganism by conjugative transfer.

Conjugative transfer of a plasmid can be performed by using a system usually applied to a transformation of Enterobacteriaceae microorganism. Usually, a donor microorganism containing a plasmid with oriT, the tra genes, and the mob gene, or modified to contain these, is prepared. The plasmid is then transferred to a recipient microorganism. Furthermore, if the plasmid has oriT, but does not contain the tra and/or the mob genes, then it can be transferred from a donor microorganism to a recipient microorganism through the use of a helper plasmid which does contain these genes. That is, a helper plasmid having the tra genes and/or the mob gene may be separately contained by a donor microorganism, and transformed with the oriT plasmid (Refer to J. Bacteriol., August 1995; 177 (15):4350-5). The oriT is an origin of transfer. The Mob protein is a nuclease which produces a nick at the oriT. The Tra proteins conjugatively transfer DNA to another cell by using the nick at the oriT.

Hereinafter, the method of transforming an Enterobacteriaceae microorganism with the plasmid of the present invention will be exemplified. The plasmid of the present invention which is native to *Pantoea, Erwinia*, or *Enterobacter* bacteria is typically extremely large (for example, pEA320 has a size of about 320 kbs), and therefore it is preferable to use the conjugative transfer method to transfer it to another microorganism. The *Pantoea, Erwinia*, or *Enterobacter* bacteria which naturally contain the plasmid of the present invention is herein called a donor strain, and the Enterobacteriaceae bacteria which is transformed with the plasmid of the present invention is called the recipient strain for convenience.

The conjugative transfer is preferably performed using the plasmid of the present invention and a helper plasmid, which is able to facilitate the conjugative transfer. By doing so, modification of the plasmid of the present invention can be minimized, even though modification may or may not be necessary. The helper plasmid preferably contains a mob gene and tra genes, both of which are required for conjugative transfer. Specifically, pRK2013 (available from CLONTECH and Biomedal) or a derivative thereof is preferable as the helper plasmid (refer to Proc. Natl. Acad. Sci. U.S.A., 76:1648-1652, 1979, the sequence can be obtained from NCCB Plasmids database). Furthermore, the plasmid of the present invention preferably carries a marker gene not originally present in the recipient strain so as to enable dominant selection when it is transferred into the recipient strain. The marker gene is as described above.

If the plasmid of the present invention does not have a marker gene, one can be inserted by a usual method such as homologous recombination. Hereinafter, inserting an antibiotic resistance gene into the plasmid of the present invention will be exemplified. Although the insertion position may be anywhere so long as it does not affect the replication and stability of the plasmid, specifically, the region adjacent to the acetoin/butanediol biosynthesis genes, the bud operon, can be used. First, the mutated bud gene can be amplified and cloned using the well-known overlap extension PCR method. This method uses chromosomal DNA from a donor strain as a template and PCR primers which contain a mutation and are complementary to a region of interest (Urban, A., Neukirchen, S. and Jaeger, K. E., A rapid and efficient method for site-directed mutagenesis using one-step overlap extension PCR, Nucleic Acids Res., 25, 2227-8, 1997). The cloned mutant-type bud operon is incorporated into pUT399 (pUT-Δbud), and the S17-1λpir strain having λ-pir (available from Biomedal, refer to R. Simon., et al., BIO/TECHNOLOGY, NOVEMBER 1983, 784-791 (1983)) is transformed with this plasmid. pUT399 has a R6K replication origin, a chloramphenicol resistance gene, and the mob region, which is required for conjugative transfer. The pUT399 plasmid cannot replicate in a strain which does not have the pir gene. Conjugative transfer is performed between the resulting strain and a donor strain, which results in a strain having the plasmid (pUT-Δbud) incorporated into pEA320 in the donor strain.

Hereinafter, the conjugative transfer using the aforementioned helper plasmid and an antibiotic resistance gene will be exemplified. A pRK-Tet plasmid which contains the Tn5::Tet gene was obtained by inserting a tetracycline resistence gene within Tn5 in the plasmid pRK2013. Plasmid pRK2013 has the tra genes, which are required for conjugative transfer. These methods were accomplished using Transposomics™ &EZ::TN™ of Epicentre. Conjugative transfer of pRK-Tet to the donor strain is perfomed. pRK-Tet is transferred into the donor strain from an *E. coli* strain which had been transformed with the pRK-Tet. Then, this donor strain containing pRK-Tet and an Enterobacteriaceae bacteria (the recipient strain) are conjugated, and selection can be performed on the basis of the chloramphenicol resistance to obtain a recipient strain having the plasmid of the present invention.

<2> Method for Utilizing the Plasmid of the Present Invention (2-1) Utilization as Vector When an objective gene is inserted at any position in the plasmid of the present invention, and a host microorganism is transformed with the obtained recombinant plasmid in a conventional manner, it is possible to express the objective gene in the host microorganism. Furthermore, a region required for replication in another host can be inserted to prepare a shuttle vector.

The host microorganism may be any microorganism, so long as it belongs to the Enterobacteriaceae bacteria family, and can produce a useful substance. The useful substance is not particularly limited, so long as it is able to be produced by a microorganism. Examples include, for example, proteins, amino acids, nucleic acids, vitamins, saccharides, organic acids, lipids, and so forth. Furthermore, the objective gene is preferably relevant to the aforementioned useful substance, and includes, for example, genes which encode a useful substance, such as a protein, genes involved in biosynthesis systems of amino acids, nucleic acids, vitamins, saccharides, organic acids, lipids, and so forth.

Examples of L-amino acids include L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine, and examples of the host microorganism therefore include L-amino acid-producing Enterobacteriaceae bacteria, such as *Escherichia coli* and *Pantoea ananatis* (European Patent Publication No. 1078989 A, U.S. Pat. No. 6,331,419).

For example, L-glutamic acid-producing bacteria include the following microorganisms:

*Pantoea ananatis* AJ13601 (FERM BP-7207)

*Klebsiella planticola* AJ13410 (FERM BP-6617)

*Pantoea ananatis* AJ13355 (FERM BP-6614)

*Erwinia herbicola* IAM1595/RSFCPG (refer to U.S. Pat. No. 6,197,559)

*Klebsiella planticola* AJ13399/RSFCPG (refer to U.S. Pat. No. 6,197,559)

*Serratia liquefaciens* ATCC14460/RSFCPG (refer to U.S. Pat. No. 6,331,419)

*Escherichia coli* AJ12628 (Japanese Patent Application Laid-open No. H05-244970)

*Escherichia coli* AJ12624 (Japanese Patent Application Laid-open No. H05-244970)

The *Pantoea ananatis* AJ13601 strain was deposited at the International Patent Organism Depositary, National Institute of Advanced Industrial Science and Technology (Central 6, 1-1-1 Higashi, Tsukuba, Ibaraki 305-8566, Japan) (former National Institute of Bioscience and Human-Technology, Agency of Industrial Science and Technology, Ministry of Economy, Trade and Industry) on Aug. 18, 1999 and given an accession number of FERM P-17516. Then, the deposit was converted to an international deposit under the provisions of the Budapest Treaty on Jul. 6, 2000 and given an accession number of FERM BP-7207. The *Pantoea ananatis* AJ13355 and AJ13356 strains were deposited at the International Patent Organism Depositary, National Institute of Advanced Industrial Science and Technology (Central 6, 1-1-1 Higashi, Tsukuba, Ibaraki 305-8566, Japan) (former National Institute of Bioscience and Human-Technology, Agency of Industrial Science and Technology, Ministry of Economy, Trade and Industry) on Feb. 19, 1998 and given accession numbers of FERM P-16644 and FERM P-16645, respectively. Then, the deposits were converted to international deposits under the provisions of the Budapest Treaty on Jan. 11, 1999 and given accession numbers of FERM BP-6614 and FERM BP-6615, respectively.

Examples of organic acids include D-gluconic acid, 2-keto-D-gluconic acid, 2,5-diketo-D-gluconic acid, and succinic acid, and examples of the host microorganism thereof include *Pantoea, Erwinia, Enterobacter* (International Publication Nos. WO98/59504, WO02/12468 etc.), and *Escherichia* bacteria (WO99/06532 etc.) (U.S. Pat. No. 6,448,061). Furthermore, examples of vitamins or precursors of vitamins include carotenoids, pantothenic acid, and ascorbic acid, and examples of the host microorganism thereof include *Pantoea* and *Escherichia* bacteria (International Publication No. WO02/072855).

Furthermore, to use the plasmid of the present invention as a vector, a multi-cloning restriction site may be introduced to facilitate insertion of an objective gene, or a potent promoter at a site upstream from the objective gene and a potent terminator at a site downstream from the objective gene may be introduced. Furthermore, the plasmid of the present invention may also be used as an expression vector that can express a protein containing a tag at an appropriate position for affinity purification of the protein.

A useful substance can be obtained by transforming, with the plasmid of the present invention, an Enterobacteriaceae microorganism which is able to produce the useful substance, culturing it in a medium under conditions which enable production of the useful substance in the medium or in the microorganism, and collecting the useful substance from the medium or the microorganism.

Mediums which are conventionally used in the production of a useful substance by fermentation of a microorganism can be used. That is, usual mediums containing a carbon source, a nitrogen source, inorganic ions, and other organic components, if needed, can be used. As the carbon source, saccharides such as glucose, sucrose, lactose, galactose, fructose, and hydrolysate of starch, alcohols such as glycerol and sorbitol, and organic acids such as fumaric acid, citric acid, and succinic acid can be used. As the nitrogen source, inorganic ammonium salts such as ammonium sulfate, ammonium chloride and ammonium phosphate, organic nitrogens such as soybean hydrolysate, ammonia gas, and aqueous ammonia can be used. As organic trace amount nutrients, it is preferable to add an appropriate amount of required substances such as vitamin $B_1$ and L-lysine or yeast extract etc. Other than these, potassium phosphate, magnesium sulfate, iron ions, manganese ions and so forth are added in a small amount as required. In addition, the medium used for the present invention may be a natural or synthetic medium, so long as the medium contains a carbon source, a nitrogen source, inorganic ions, and other organic trace amount components, as required.

The culture is usually carried out for 1 to 7 days under aerobic conditions. The culture temperature is usually 24 to 37° C., and pH during the culture is usually 5 to 9. For pH control, inorganic or organic, acidic or alkaline substances, ammonia gas etc. can be used. When the useful substance is produced and excreted from the microorganism, precipitates such as cells are removed from the culture after completion of the culture, and then the useful substance can be isolated and purified by a combination of known methods, such as ion exchange, precipitation, and other methods. In addition, when the useful substance accumulates within the microorganism, for example, the cell can be disrupted by ultrasonication or the like, and the useful substance can be collected by the ion exchange resin method or the like from the supernatant after centrifugal separation or the like.

Furthermore, the plasmid of the present invention or a derivative thereof may also be used as a vector to disrupt an objective gene of an Enterobacteriaceae microorganism. For example, such a mutation can be introduced into the amino acid sequence of SEQ ID NO: 2, so that that the plasmid can replicate at a low culture temperature, but cannot replicate at a high temperature, and homologous recombination is induced between a DNA fragment of the mutant gene and a gene having a homologous sequence and existing on a chromosome of an Enterobacteriaceae microorganism. Such manipulations result in an Enterobacteriaceae microorganism which has the DNA fragment incorporated into the chromosome. To make the plasmid of the present invention temperature sensitive, for example, treating the DNA with hydroxyamine results in a plasmid having a mutation that makes the plasmid autonomously replicable at a low temperature, but not replicable at a high temperature (refer to U.S. Pat. No. 6,303,383).

(2-2) Imparting Acid Resistance

The plasmid of the present invention which is native to *Pantoea*, *Erwinia* or *Enterobacter* bacteria is able to increase the acid resistance of a microorganism. The plasmid of the present invention is also suitable to increase acid resistance of a microorganism, other than the aforementioned use as a vector, so long as it is modified so that the effect of increasing acid resistance of a microorganism is not degraded.

In the present invention, "increasing acid resistance" means that when a microorganism containing the plasmid of the present invention is cultured under acidic conditions, the growth rate is improved or the critical pH for growth is lowered, as compared with the parent strain which does not contain the plasmid of the present invention. Examples of the parent strain include wild-type strains, for example, the *Escherichia coli* MG1655 strain, and so forth. In this case, the pH in the medium is 6 or lower, preferably 5.5 or lower, more preferably 4.9 or lower. Although the lower limit of pH is not limited so long as growth is possible due to the transformation with the plasmid of the present invention, it is, for example, 3 or higher.

Examples of the method to compare the growth with that of the parent strain include measuring absorbances of culture mediums in which a parent strain and the inventive strain have been cultured at a wavelength from 580 to 660 nm, and comparing the absorbances.

In addition, when the plasmid of the present invention is used to impart acid resistance as described above, it may concomitantly be used as a vector. That is, when a strain containing the plasmid of the present invention carrying an objective gene is used, growth of the strain under acidic conditions is improved, and productivity of a useful substance may also be improved.

Hereinafter, the present invention will be further explained with reference to the following non-limiting examples.

EXAMPLE 1

Since pEA320 is extremely large (about 320 kbs), it is difficult to isolate as a cyclic DNA and difficult to use to transform a strain. Furthermore, since neither a drug resistance gene nor a marker enabling dominant selection exists on this plasmid, a marker gene must be introduced which enables dominant selection. Therefore, pUT399 was constructed so that homologous recombination could occur, and, as a result, a strain could be selected using chloramphenicol (U.S. Patent Application Publication No. 20040180404).

pUT399 was constructed as follows. PCR was conducted using pUT-miniTn5-Cm (which can be purchased from Biomedal) as a template, and P7 (SEQ ID NO: 9) and P8 (SEQ ID NO: 10) as primers, resulting in amplification of the replication origin of R6K and the mob gene of RP4. Furthermore, when pHSG399 (TaKaRa) was used as a template, and P9 (SEQ ID NO: 11) and P10 (SEQ ID NO: 12) as primers, the region containing a chloramphenicol resistance gene and a multi-cloning site was amplified. These were treated with the restriction enzyme BglII, respectively, and then ligated by using T4 DNA ligase.

pUT399 contains the replication origin of R6K and the mob region required for conjugative transfer. Furthermore, pUT399 cannot replicate in a strain lacking the pir gene. Therefore, by constructing a plasmid carrying a sequence which exists in pEA320 on pUT399, transforming *P. ananatis* with it by conjugation, and performing selection with chloramphenicol, a strain of *P. ananatis* can be obtained which contains a plasmid in which recombination is caused in a homologous region, and thus pUT399 is introduced into pEA320.

The specific procedure will be described below. Although isolation of pEA320 is difficult by the usual alkali-SDS method due to the extremely large size of the plasmid (320 kbs), it can be collected with chromosomes during the isolation of chromosomes in a conventional manner. In this experiment, the gene of the budAB operon was chosen as a gene on pEA320. To delete about 370 bps downstream from budA and about 500 bps upstream from the budB gene, primers P1 (SEQ ID NO: 3) and P2 (SEQ ID NO: 4), or P3 (SEQ ID NO: 5) and P4 (SEQ ID NO: 6) were synthesized and used together with chromosomes of the AJ13355 strain (FERM BP-6614) as a template to perform the first PCR. Then, a fragment of about 2.3 kbs was amplified by overlap extension PCR using the aforementioned PCR product as a template and primers P5 (SEQ ID NO: 7) and P6 (SEQ ID NO: 8). Then, the obtained amplified fragment was incorporated into pCR2.1 (Invitrogen), and this plasmid was treated with EcoRI to obtain an insertion fragment having an EcoRI site. Finally, this fragment was incorporated into pUT399 which had been treated with EcoRI, and used to transform the S17-1λpir strain (which can be purchased from Biomedal, refer to Simon., R., et al., BIO/TECHNOLOGY, NOVEMBER 1983, 784-791 (1983)).

The obtained strain, S17-1λpir/pUT-Δbud strain, and the *P. ananatis* NP106 strain were conjugated to obtain a NP106/pEA320-bud::Cm strain, in which pUT-Δbud was incorporated by homologous recombination into a gene region on pEA320. The *P. ananatis* NP106 strain is obtained by eliminating the native plasmids RSFCPG and pSTVCB from the *Pantoea ananatis* AJ13601 strain (FERM BP-7207 strain). In this construction, the full length budAB gene and a disrupted-type budAB gene, as well as the total region of pUT399, were incorporated into pEA320. Then, the *E. coli* DH5α strain (produced by TaKaRa Bio), which has the pRK-Tet plasmid was used as a donor strain, and the pRK-Tet plasmid was transferred into the NP106/pEA320-bud::Cm strain by conjugation. The pRK-Tet plasmid was constructed by introducing Tn5::Tet gene into pRK2013 (Biomedal), which has the tra genes required for conjugative transfer. The construction was performed by using Transposomics™ &EZ::TN™ of Epicentre. Then, this NP106/pEA320-bud::Cm, pRK-Tet strain and the MG1655 strain were conjugated, and by selection on the M9 glucose agar medium containing 25 mg/L of chloramphenicol, an MG1655, pEA320-bud::Cm strain containing the transferred pEA320 was obtained.

EXAMPLE 2

<Growth of *E. coli* Containing pEA320 Under Acidic Conditions>

Growth of the *E. coli* MG1655 strain containing pEA320 under acidic conditions was examined.

Specifically, the wild-type strain MG1655 and the pEA320-transformed strain, MG1655/pEA320-bud::Cm, were separately precultured in L medium (10 g of Bacto tryptone, 5 g of yeast extract, 5 g of NaCl and 15 g of agar in 1 L of purified water, pH 7.0), wherein the pEA320-transformed strain culture was supplemented with 25 mg/L of chloramphenicol. Then the cells were washed twice with sterilized water and inoculated into the M9 minimal medium (2 mM magnesium sulfate, 3 g of monopotassium phosphate, 0.5 g of sodium chloride, 1 g of ammonium chloride and 6 g of disodium phosphate in 1 L of purified water) containing 30 g/L of glutamic acid and 5 g/L of glucose and adjusted to pH 7.0 or 4.5 with aqueous ammonia at a density of OD 660 nm=0.05. The OD of the medium was measured over time. For the culture and OD measurement, TN1506 produced by ADVANTEC was used.

Figure 6:
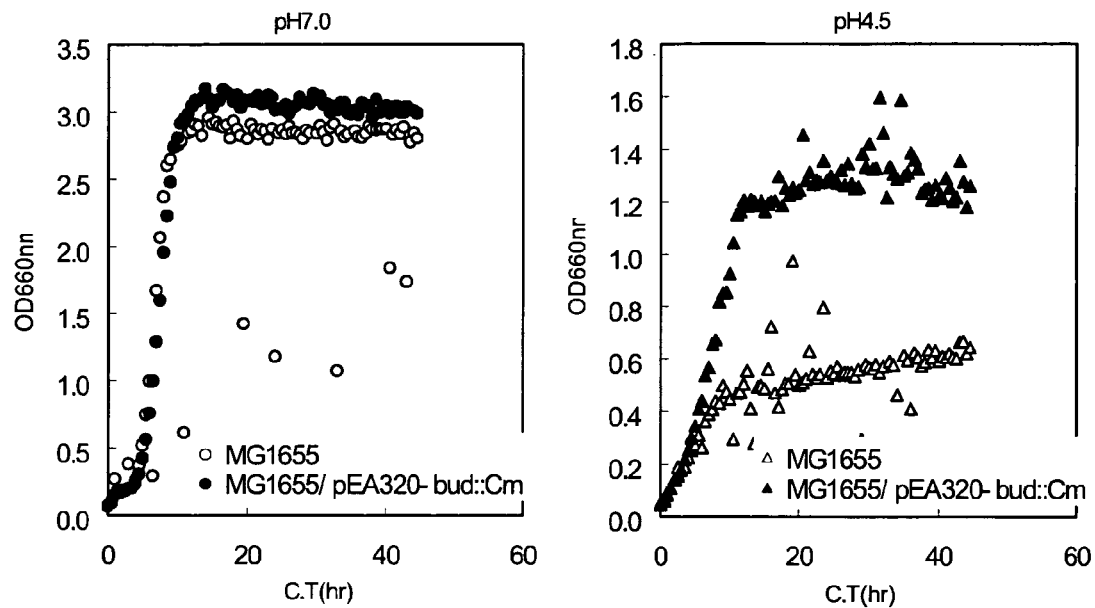
FIG. 6 shows graphs indicating growth of the plasmid pEA320-transformed *E. coli* under neutral and acidic conditions.

As shown in FIG. 6, whereas almost no difference in growth was seen at pH 7.0, growth was markedly improved at pH 4.5. That is, pEA320 imparts acid resistance.

Then, in order to analyze this phenomenon in more detail, the culture under pH-controlled conditions using a jar fermenter was performed. The wild-type strain MG1655 and the pEA320-transformed strain, MG1655/pEA320-bud::Cm, were each separately precultured in L medium (10 g of Bacto tryptone, 5 g of yeast extract, 5 g of NaCl and 15 g of agar in 1 L of purified water, pH 7.0), wherein the pEA320-transformed strain culture was supplemented with 25 mg/L of chloramphenicol. The cells on one plate for each were inoculated into 300 mL of a medium having the composition shown below charged in a jar fermenter. The culture was performed at 37° C. and pH 4.9 or 4.7 with aeration of 1/1 vvm and oxygen concentration of 5% or higher at 34° C., which were controlled by stirring, and pH was adjusted to 4.9 and 4.7 by addition of ammonia gas during the culture.

Figure 7:
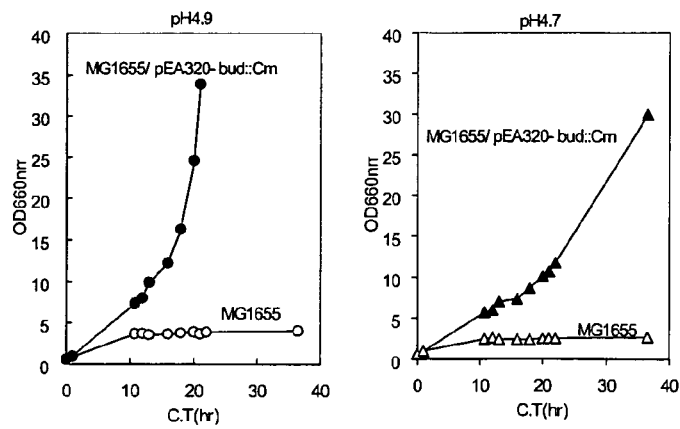
FIG. 7 shows graphs indicating growth of the plasmid pEA320-transformed *E. coli* under acidic conditions.

As shown in FIG. 7, the MG1655 containing pEA320 could grow even at pH 4.7 and 4.9, and MG1655 cannot grow at these pHs. Thus it was confirmed that transformation with pEA320 improved the acid resistance.

TABLE 2

| Medium composition for main culture | |
|---|---|
| Glucose | 50 g/L |
| $(NH_4)_2SO_4$ | 5.0 g/L |
| $MgSO_4 \cdot 7H_2O$ | 0.4 g/L |
| GD113 | 0.1 mL/L |
| Yeast extract | 6.0 g/L |
| $KH_2PO_4$ | 6.0 g/L |
| NaCl | 1.5 g/L |
| $FeSO_4 \cdot 7H_2O$ | 0.02 g/L |
| $MnSO_4 \cdot 5H_2O$ | 0.02 g/L |
| Chloramphenicol | 25 mg/L |
| Calcium chloride dihydrate | 0.75 g/L |

INDUSTRIAL APPLICABILITY

According to the present invention, a novel plasmid useful for breeding and improving Enterobacteriaceae microorganisms is provided. The plasmid of the present invention can be used for breeding of Enterobacteriaceae microorganisms and used to produce useful substances, and can improve growth of the microorganisms under acidic conditions.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

We claim:

1. A gene isolated from a microorganism selected from the group consisting of *Pantoea* bacteria, *Erwinia* bacteria, and *Enterobacter* bacteria, wherein said gene encodes a Rep protein having the amino acid sequence selected from the group consisting of the amino acid sequence of SEQ ID NO: 2, and an amino acid sequence which is at least 95% homologous to SEQ ID NO: 2.

2. A plasmid comprising the gene according to claim 1, wherein said plasmid is autonomously replicable in Enterobacteriaceae bacteria.

3. The plasmid according to claim 2, which further comprises a marker gene.

4. The plasmid according to claim 2, wherein the plasmid is from a *Pantoea* bacterium selected from the group consisting of *Pantoea ananatis* FERM BP-7207, BP-6614, and BP-6615, and is about 320 kbs.

5. The plasmid according to claim 2, wherein the plasmid is pEA320, and has a restriction enzyme map selected from the group consisting of those shown in FIGS. 1, 2, 3, 4, and 5.

6. An Enterobacteriaceae microorganism which has been transformed with a plasmid comprising a gene isolated from a microorganism selected from the group consisting of *Pantoea* bacteria, *Erwinia* bacteria, and *Enterobacter* bacteria, and wherein said gene encodes a Rep protein having the amino acid sequence selected from the group consisting of the amino acid sequence of SEQ ID NO: 2, and an amino acid sequence which is at least 95% homologous to SEQ ID NO: 2.

7. The microorganism according to claim 6, wherein the plasmid is from a *Pantoea* bacterium selected from the group consisting of *Pantoea ananatis* FERM BP-7207, BP-6614, and BP-6615, and is about 320 kbs.

8. The microorganism according to claim 6, wherein the plasmid is pEA320, and has a restriction enzyme map selected from the group consisting of those shown in FIGS. 1, 2, 3, 4, and 5.

9. The microorganism according to claim 6, wherein the plasmid further comprises a marker gene and is autonomously replicable in an Enterobacteriaceae microorganism.

10. The microorganism according to claim 6, wherein the Enterobacteriaceae microorganism is selected from the group consisting of *Escherichia* bacteria, *Pantoea* bacteria, *Enterobacter* bacteria *Erwinia* bacteria, *Klebsiella* bacteria, *Serratia* bacteria, *Salmonella* bacteria, and *Morganella* bacteria.

11. The microorganism according to claim 6, which produces an amino acid.

12. A method for producing an amino acid comprising culturing the microorganism according to claim 11 in a medium, and collecting the amino acid from the medium or the microorganism.

13. A method for producing a microorganism with improved acid resistance comprising transforming an Enterobacteriaceae microorganism with the plasmid according to claim 4.

14. The method according to claim 13, wherein the microorganism with improved acid resistance shows improved growth at a pH of 3 to 5, as compared with a strain not containing the plasmid.

* * * * *

SEQUENCE LISTING

<160> NUMBER OF SEQ ID NOS: 12

<210> SEQ ID NO 1
<211> LENGTH: 930
<212> TYPE: DNA
<213> ORGANISM: Pantoea ananatis
<220> FEATURE:
<221> NAME/KEY: CDS
<222> LOCATION: (1)..(927)

<400> SEQUENCE: 1

```
atg gca gat aaa gat agt gaa aac aaa gcg tta cta gag cct ttt ctg      48
Met Ala Asp Lys Asp Ser Glu Asn Lys Ala Leu Leu Glu Pro Phe Leu
1               5                   10                  15 tct gtg acc aaa aac agt ggt gaa gtt att cag ctt cat ccc aac aaa      96
Ser Val Thr Lys Asn Ser Gly Glu Val Ile Gln Leu His Pro Asn Lys
                20                  25                  30 aat aat acc gtt cag ccc gtg gcc tta atg cgt ctg gga ctc ttt gtt     144
Asn Asn Thr Val Gln Pro Val Ala Leu Met Arg Leu Gly Leu Phe Val
            35                  40                  45 ccc acg ctt aaa tcc aca gcg cgg ggc att tct ggt gct atg gct tca     192
Pro Thr Leu Lys Ser Thr Ala Arg Gly Ile Ser Gly Ala Met Ala Ser
        50                  55                  60 acc gat gcc acc aaa gag ctt aaa aac ctc tct ctg gtt aaa gcg gaa     240
Thr Asp Ala Thr Lys Glu Leu Lys Asn Leu Ser Leu Val Lys Ala Glu
65                  70                  75                  80 ggt tat gaa aag att acc atc acc ggt gcc aga ctg gat atg gat aat     288
Gly Tyr Glu Lys Ile Thr Ile Thr Gly Ala Arg Leu Asp Met Asp Asn
                85                  90                  95 gac ttt aag acc tgg gcc ggt att att cag tct ttt tcc cgt tac cct     336
Asp Phe Lys Thr Trp Ala Gly Ile Ile Gln Ser Phe Ser Arg Tyr Pro
                100                 105                 110 aca cag ggt gat acg gta acc ctg cct ttt att gat ttc gtg aag atg     384
Thr Gln Gly Asp Thr Val Thr Leu Pro Phe Ile Asp Phe Val Lys Met
            115                 120                 125 tgc ggt att ccc tcc gcc aac tcc tct gcc gca ttg cgt aag cga ctc     432
Cys Gly Ile Pro Ser Ala Asn Ser Ser Ala Ala Leu Arg Lys Arg Leu
        130                 135                 140 gac gct tcg tta cgc cgt att gcg acg aac act ctc tct ttt gaa ggt     480
Asp Ala Ser Leu Arg Arg Ile Ala Thr Asn Thr Leu Ser Phe Glu Gly
145                 150                 155                 160 aac ggt aag gcc tat cat acg cat ctg gta cag tca gct tat tac gat     528
Asn Gly Lys Ala Tyr His Thr His Leu Val Gln Ser Ala Tyr Tyr Asp
                165                 170                 175 cgt gaa aaa gac att gtc cgc ata cag gct gat ccc aag ctc ttt gag     576
Arg Glu Lys Asp Ile Val Arg Ile Gln Ala Asp Pro Lys Leu Phe Glu
                180                 185                 190 ctg tat aac ttc gac cac aag gtt tta ctg cag ctg agg gct atc tcc     624
Leu Tyr Asn Phe Asp His Lys Val Leu Leu Gln Leu Arg Ala Ile Ser
            195                 200                 205 cgc ctt aag cgt aaa gaa tcg gct cag gcg ctt tat acg ttc ctg gag     672
Arg Leu Lys Arg Lys Glu Ser Ala Gln Ala Leu Tyr Thr Phe Leu Glu
        210                 215                 220 agc ctg ccg acc aac cct gcg ccc att tct ctt gcc cgc tta cgt atg     720
Ser Leu Pro Thr Asn Pro Ala Pro Ile Ser Leu Ala Arg Leu Arg Met
225                 230                 235                 240 cgg ctc aat ctt ggc tca aag att acc acg cag aat cac gtg gta cga     768
Arg Leu Asn Leu Gly Ser Lys Ile Thr Thr Gln Asn His Val Val Arg
                245                 250                 255
```

```
cgc gcg atg gaa cag ctt aaa gag att ggc tac ctt gat tac tct gaa      816
Arg Ala Met Glu Gln Leu Lys Glu Ile Gly Tyr Leu Asp Tyr Ser Glu
        260                 265                 270 gtc aaa cga ggc cgc tcc gta ttt ttc atc att cac agc aga aca ccg      864
Val Lys Arg Gly Arg Ser Val Phe Phe Ile Ile His Ser Arg Thr Pro
            275                 280                 285 aaa ctc gat gga atc agt aac ctg gaa gga atc gat acg ctc gat gac      912
Lys Leu Asp Gly Ile Ser Asn Leu Glu Gly Ile Asp Thr Leu Asp Asp
290                 295                 300 atc gat ttt gaa gac tga                                              930
Ile Asp Phe Glu Asp
305
```

<210> SEQ ID NO 2
<211> LENGTH: 309
<212> TYPE: PRT
<213> ORGANISM: Pantoea ananatis

<400> SEQUENCE: 2

```
Met Ala Asp Lys Asp Ser Glu Asn Lys Ala Leu Leu Glu Pro Phe Leu
1               5                   10                  15

Ser Val Thr Lys Asn Ser Gly Glu Val Ile Gln Leu His Pro Asn Lys
            20                  25                  30

Asn Asn Thr Val Gln Pro Val Ala Leu Met Arg Leu Gly Leu Phe Val
        35                  40                  45

Pro Thr Leu Lys Ser Thr Ala Arg Gly Ile Ser Gly Ala Met Ala Ser
    50                  55                  60

Thr Asp Ala Thr Lys Glu Leu Lys Asn Leu Ser Leu Val Lys Ala Glu
65                  70                  75                  80

Gly Tyr Glu Lys Ile Thr Ile Thr Gly Ala Arg Leu Asp Met Asp Asn
                85                  90                  95

Asp Phe Lys Thr Trp Ala Gly Ile Ile Gln Ser Phe Ser Arg Tyr Pro
            100                 105                 110

Thr Gln Gly Asp Thr Val Thr Leu Pro Phe Ile Asp Phe Val Lys Met
        115                 120                 125

Cys Gly Ile Pro Ser Ala Asn Ser Ser Ala Ala Leu Arg Lys Arg Leu
    130                 135                 140

Asp Ala Ser Leu Arg Arg Ile Ala Thr Asn Thr Leu Ser Phe Glu Gly
145                 150                 155                 160

Asn Gly Lys Ala Tyr His Thr His Leu Val Gln Ser Ala Tyr Tyr Asp
                165                 170                 175

Arg Glu Lys Asp Ile Val Arg Ile Gln Ala Asp Pro Lys Leu Phe Glu
            180                 185                 190

Leu Tyr Asn Phe Asp His Lys Val Leu Leu Gln Leu Arg Ala Ile Ser
        195                 200                 205

Arg Leu Lys Arg Lys Glu Ser Ala Gln Ala Leu Tyr Thr Phe Leu Glu
    210                 215                 220

Ser Leu Pro Thr Asn Pro Ala Pro Ile Ser Leu Ala Arg Leu Arg Met
225                 230                 235                 240

Arg Leu Asn Leu Gly Ser Lys Ile Thr Thr Gln Asn His Val Val Arg
                245                 250                 255

Arg Ala Met Glu Gln Leu Lys Glu Ile Gly Tyr Leu Asp Tyr Ser Glu
            260                 265                 270

Val Lys Arg Gly Arg Ser Val Phe Phe Ile Ile His Ser Arg Thr Pro
        275                 280                 285

Lys Leu Asp Gly Ile Ser Asn Leu Glu Gly Ile Asp Thr Leu Asp Asp
```

```
             290              295              300
Ile Asp Phe Glu Asp
305

<210> SEQ ID NO 3
<211> LENGTH: 30
<212> TYPE: DNA
<213> ORGANISM: Artificial sequence
<220> FEATURE:
<223> OTHER INFORMATION: primer

<400> SEQUENCE: 3
gcgcgcaaac aggcaactga caataagctc                                    30

<210> SEQ ID NO 4
<211> LENGTH: 48
<212> TYPE: DNA
<213> ORGANISM: Artificial sequence
<220> FEATURE:
<223> OTHER INFORMATION: primer

<400> SEQUENCE: 4
cggctgatca acgatatcct gtgggtgcac aaaactggtt gtcggagg                48

<210> SEQ ID NO 5
<211> LENGTH: 23
<212> TYPE: DNA
<213> ORGANISM: Artificial sequence
<220> FEATURE:
<223> OTHER INFORMATION: primer

<400> SEQUENCE: 5
ccacaggata tcgttgatca gcc                                           23

<210> SEQ ID NO 6
<211> LENGTH: 30
<212> TYPE: DNA
<213> ORGANISM: Artificial sequence
<220> FEATURE:
<223> OTHER INFORMATION: primer

<400> SEQUENCE: 6
ttaaagtaac tggctgagat gaagctgccc                                    30

<210> SEQ ID NO 7
<211> LENGTH: 24
<212> TYPE: DNA
<213> ORGANISM: Artificial sequence
<220> FEATURE:
<223> OTHER INFORMATION: primer

<400> SEQUENCE: 7
gacaataagc tcatacagac tggg                                          24

<210> SEQ ID NO 8
<211> LENGTH: 23
<212> TYPE: DNA
<213> ORGANISM: Artificial sequence
<220> FEATURE:
<223> OTHER INFORMATION: primer

<400> SEQUENCE: 8
ccatcagcaa gtggttatcg gcg                                           23

<210> SEQ ID NO 9
```

-continued

```
<211> LENGTH: 30
<212> TYPE: DNA
<213> ORGANISM: Artificial sequence
<220> FEATURE:
<223> OTHER INFORMATION: primer

<400> SEQUENCE: 9
tcatagatct tttagattga tttatggtgc                                              30

<210> SEQ ID NO 10
<211> LENGTH: 30
<212> TYPE: DNA
<213> ORGANISM: Artificial sequence
<220> FEATURE:
<223> OTHER INFORMATION: primer

<400> SEQUENCE: 10
ccacagatct aattcccatg tcagccgtta                                              30

<210> SEQ ID NO 11
<211> LENGTH: 30
<212> TYPE: DNA
<213> ORGANISM: Artificial sequence
<220> FEATURE:
<223> OTHER INFORMATION: primer

<400> SEQUENCE: 11
ataaagatct gtgtccctgt tgataccggg                                              30

<210> SEQ ID NO 12
<211> LENGTH: 30
<212> TYPE: DNA
<213> ORGANISM: Artificial sequence
<220> FEATURE:
<223> OTHER INFORMATION: primer

<400> SEQUENCE: 12
ggggagatct tgcaaggcga ttaagttggg                                              30
```